(12) United States Patent
Fenlon et al.

(10) Patent No.: US 12,370,310 B2
(45) Date of Patent: Jul. 29, 2025

(54) MEDICAMENT CONTAINER CARRIER AND ADAPTER

(71) Applicant: Sanofi-Aventis Deutschland GMBH, Frankfurt am Main (DE)

(72) Inventors: Derek Fenlon, Wexford (IE); Pascal Launois, Dublin (IE); Julian McDonnell, County Wicklow (IE); Martina Moyne, County Donegal (IE); Conor Mulcahy, County Dublin (IE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 18/960,071

(22) Filed: Nov. 26, 2024

(65) Prior Publication Data
US 2025/0082854 A1    Mar. 13, 2025

Related U.S. Application Data

(63) Continuation of application No. 17/564,354, filed on Dec. 29, 2021, which is a continuation of application (Continued)

(30) Foreign Application Priority Data

Mar. 14, 2013    (EP) ..................... 13159253

(51) Int. Cl.
| A61M 5/19 | (2006.01) |
| A61J 1/20 | (2006.01) |
| A61M 5/31 | (2006.01) |

(52) U.S. Cl.
CPC .............. *A61M 5/19* (2013.01); *A61J 1/2096* (2013.01); *A61M 5/3129* (2013.01); *A61J 1/201* (2015.05)

(58) Field of Classification Search
None
See application file for complete search history.

(56) References Cited

U.S. PATENT DOCUMENTS

| 3,026,873 A | 3/1962 | Miskel et al. |
| 3,076,455 A | 2/1963 | McConnaughey et al. |
| (Continued) |

FOREIGN PATENT DOCUMENTS

| CA | 2212489 A1 | 2/1998 |
| CN | 2745588 Y | 12/2005 |
| (Continued) |

OTHER PUBLICATIONS

International Preliminary Report on Patentability in International Appln. No. PCT/EP2014/054922, issued on Sep. 15, 2015, 6 pages.
(Continued)

*Primary Examiner* — Manuel A Mendez
(74) *Attorney, Agent, or Firm* — Fish & Richardson P.C.

(57) ABSTRACT

Described is a medicament container carrier adapted to hold a first medicament container having a first predetermined size and capable of containing more than a first volume of a medicament. The container carrier comprises a body, and an adapter coupled to the body. The adapter is adapted to hold a second medicament container having a second predetermined size different from the first predetermined size and capable of containing no more than the first volume of the medicament.

30 Claims, 6 Drawing Sheets

Related U.S. Application Data

No. 14/775,316, filed as application No. PCT/EP2014/054922 on Mar. 13, 2014, now Pat. No. 11,235,102.

(56) References Cited

U.S. PATENT DOCUMENTS

| | | |
|---|---|---|
| 3,144,178 A | 8/1964 | Sarnoff |
| 3,880,163 A | 4/1975 | Ritterskamp |
| 4,563,175 A | 1/1986 | Lafond |
| 4,643,724 A | 2/1987 | Jobe |
| 4,655,751 A | 4/1987 | Harbaugh |
| 4,664,653 A | 5/1987 | Sagstetter et al. |
| 4,735,311 A | 4/1988 | Lowe et al. |
| 4,838,857 A | 6/1989 | Strowe et al. |
| 4,871,355 A | 10/1989 | Kikkawa |
| 4,909,791 A | 3/1990 | Norelli |
| 4,931,040 A | 6/1990 | Haber et al. |
| 4,946,447 A | 8/1990 | Hardcastle et al. |
| 4,964,866 A | 10/1990 | Szwarc |
| 4,973,318 A | 11/1990 | Holm et al. |
| 4,990,142 A | 2/1991 | Hoffman et al. |
| 4,997,422 A | 3/1991 | Chow et al. |
| 5,000,744 A | 3/1991 | Hoffman et al. |
| 5,078,698 A | 1/1992 | Stiehl et al. |
| 5,085,641 A | 2/1992 | Sarnoff et al. |
| 5,163,918 A | 11/1992 | Righi et al. |
| 5,169,392 A | 12/1992 | Ranford et al. |
| 5,281,198 A | 1/1994 | Haber et al. |
| 5,282,793 A | 2/1994 | Larson |
| 5,290,255 A | 3/1994 | Vallelunga et al. |
| 5,320,609 A | 6/1994 | Haber et al. |
| 5,322,511 A | 6/1994 | Armbruster et al. |
| 5,344,407 A | 9/1994 | Ryan |
| 5,350,367 A | 9/1994 | Stiehl et al. |
| 5,356,395 A | 10/1994 | Chen |
| 5,368,578 A | 11/1994 | Covington et al. |
| 5,383,858 A | 1/1995 | Reilly et al. |
| 5,383,863 A | 1/1995 | Mardones |
| 5,439,450 A | 8/1995 | Haedt |
| 5,451,214 A | 9/1995 | Hajishoreh |
| 5,480,387 A | 1/1996 | Gabriel et al. |
| 5,520,653 A | 5/1996 | Reilly et al. |
| 5,599,309 A | 2/1997 | Marshall et al. |
| 5,637,101 A | 6/1997 | Shillington |
| 5,709,662 A | 1/1998 | Olive et al. |
| 5,779,675 A | 7/1998 | Uber et al. |
| 5,865,805 A | 2/1999 | Ziemba |
| 5,913,844 A | 6/1999 | Fago et al. |
| 5,925,032 A | 7/1999 | Clements |
| 5,928,205 A | 7/1999 | Marshall |
| 5,928,698 A | 7/1999 | Soyad |
| 6,059,756 A | 5/2000 | Yeh |
| 6,090,082 A | 7/2000 | King et al. |
| 6,203,530 B1 | 3/2001 | Stewart |
| 6,210,369 B1 | 4/2001 | Wilmot et al. |
| 6,371,939 B2 | 4/2002 | Bergens et al. |
| 6,409,701 B1 | 6/2002 | Cohn et al. |
| 6,454,743 B1 | 9/2002 | Weber |
| 6,544,234 B1 | 4/2003 | Gabriel |
| 6,613,022 B1 | 9/2003 | Doyle |
| 6,656,163 B1 | 12/2003 | Marshall et al. |
| 6,726,657 B1 | 4/2004 | Dedig et al. |
| 6,743,205 B2 | 6/2004 | Nolan, Jr. et al. |
| 7,118,552 B2 | 10/2006 | Shaw et al. |
| 7,288,078 B2 | 10/2007 | Fitzgerald |
| 7,449,012 B2 | 11/2008 | Young et al. |
| 7,597,685 B2 | 10/2009 | Olson |
| 7,717,877 B2 | 5/2010 | Lavi et al. |
| 7,918,824 B2 | 4/2011 | Bishop et al. |
| 7,955,303 B2 | 6/2011 | Burren et al. |
| 8,409,138 B2 | 4/2013 | James et al. |
| 8,647,299 B2 | 2/2014 | Stamp |
| 8,734,394 B2 | 5/2014 | Admas et al. |
| 8,845,594 B2 | 9/2014 | Jennings |
| 8,876,785 B2 | 11/2014 | Holmqvist |
| 8,900,197 B2 | 12/2014 | Crow |
| 8,992,746 B2 | 3/2015 | Miyaji et al. |
| 9,044,553 B2 | 6/2015 | James et al. |
| 9,072,833 B2 | 7/2015 | Jennings et al. |
| 9,180,259 B2 | 11/2015 | Lesch, Jr. |
| 9,216,256 B2 | 12/2015 | Olson et al. |
| 9,233,213 B2 | 1/2016 | Olson et al. |
| 9,242,053 B2 | 1/2016 | Wozencroft |
| 9,289,554 B2 | 3/2016 | Hourmand et al. |
| 9,402,957 B2 | 8/2016 | Adams et al. |
| 9,408,970 B2 | 8/2016 | Hourmand et al. |
| 9,408,976 B2 | 8/2016 | Olson et al. |
| 9,713,678 B2 | 7/2017 | Hourmand et al. |
| 9,757,520 B2 | 9/2017 | Corrigan |
| 9,867,940 B2 | 1/2018 | Holmqvist et al. |
| 9,872,961 B2 | 1/2018 | Fourt et al. |
| 10,118,001 B2 | 11/2018 | Fourt et al. |
| 10,314,981 B2 | 6/2019 | Sampson et al. |
| 10,350,362 B2 | 7/2019 | Dennis, Jr. et al. |
| 10,363,377 B2 | 7/2019 | Atterbury et al. |
| 10,420,898 B2 | 9/2019 | Daniel |
| 10,434,258 B2 | 10/2019 | Hourmand et al. |
| 10,441,719 B2 | 10/2019 | Hourman et al. |
| 10,569,019 B2 | 2/2020 | Hirschel et al. |
| 10,646,656 B2 | 5/2020 | Hourmand et al. |
| 10,799,647 B2 | 10/2020 | Hosteettler et al. |
| 10,881,799 B2 | 1/2021 | Hirschel et al. |
| 10,918,803 B2 | 2/2021 | Kemp et al. |
| 11,103,649 B2 | 8/2021 | Kemp et al. |
| 11,235,102 B2 * | 2/2022 | Fenlon .................... A61M 5/19 |
| 11,298,462 B2 | 4/2022 | Atterburg et al. |
| 11,383,044 B2 | 7/2022 | Tschirren et al. |
| 11,400,221 B2 | 8/2022 | Hourmand et al. |
| 11,400,222 B2 | 8/2022 | Hourmand et al. |
| 11,400,223 B2 | 8/2022 | Hourmand et al. |
| 11,406,763 B2 | 8/2022 | Hourmand et al. |
| 11,406,764 B2 | 8/2022 | Hourmand et al. |
| 11,452,821 B2 | 9/2022 | Lafever et al. |
| 11,511,043 B2 | 11/2022 | Hourmand et al. |
| 12,036,392 B1 | 7/2024 | Fenlon et al. |
| 2001/0005781 A1 | 6/2001 | Bergens et al. |
| 2001/0011163 A1 | 8/2001 | Nolan, Jr. et al. |
| 2002/0045866 A1 | 4/2002 | Sadowski et al. |
| 2002/0083564 A1 | 7/2002 | James |
| 2003/0105430 A1 | 6/2003 | Lavi et al. |
| 2004/0039336 A1 | 2/2004 | Amark et al. |
| 2004/0108339 A1 | 6/2004 | Hansen et al. |
| 2005/0020979 A1 | 1/2005 | Westbye et al. |
| 2005/0027255 A1 | 2/2005 | Lavi et al. |
| 2005/0075602 A1 | 4/2005 | Cherif-Cheikh et al. |
| 2005/0075608 A1 | 4/2005 | Holdgate et al. |
| 2005/0101919 A1 | 5/2005 | Brunnberg |
| 2005/0115507 A1 | 6/2005 | Halachmi et al. |
| 2005/0165353 A1 | 7/2005 | Pessin |
| 2005/0277896 A1 | 12/2005 | Messerli et al. |
| 2006/0036216 A1 | 2/2006 | Rimlinger et al. |
| 2006/0151049 A1 | 7/2006 | Nemoto |
| 2006/0161114 A1 | 7/2006 | Perot et al. |
| 2006/0167412 A1 | 7/2006 | Marshall |
| 2006/0184133 A1 | 8/2006 | Pessin |
| 2007/0173770 A1 | 7/2007 | Stamp |
| 2007/0260348 A1 | 11/2007 | Gordils |
| 2008/0147003 A1 | 6/2008 | Menzi et al. |
| 2008/0228143 A1 | 9/2008 | Stamp |
| 2008/0262427 A1 | 10/2008 | Hommann |
| 2008/0269692 A1 | 10/2008 | James et al. |
| 2009/0012471 A1 | 1/2009 | Harrison |
| 2009/0105663 A1 | 4/2009 | Brand et al. |
| 2009/0254027 A1 | 10/2009 | Moeller |
| 2010/0152655 A1 | 6/2010 | Stamp |
| 2010/0179507 A1 | 7/2010 | Hess et al. |
| 2010/0185178 A1 | 7/2010 | Sharp et al. |
| 2011/0125100 A1 | 5/2011 | Schwirtz et al. |
| 2011/0190693 A1 | 8/2011 | Takatsuka et al. |
| 2012/0053528 A1 | 3/2012 | Bollenbach et al. |
| 2012/0130321 A1 | 5/2012 | Woehr |
| 2012/0186075 A1 | 7/2012 | Edginton |
| 2012/0203186 A1 | 8/2012 | Vogt et al. |
| 2012/0209092 A1 | 8/2012 | Alexandersson |

(56) References Cited

U.S. PATENT DOCUMENTS

| | | |
|---|---|---|
| 2012/0209192 A1 | 8/2012 | Alexandersson |
| 2013/0220869 A1 | 8/2013 | Klintenstedt et al. |
| 2014/0243753 A1 | 8/2014 | Bostrom |
| 2014/0249479 A1 | 9/2014 | Pfrang |
| 2014/0323985 A1 | 10/2014 | Hourmand et al. |
| 2014/0330203 A1 | 11/2014 | McLoughlin et al. |
| 2014/0330213 A1 | 11/2014 | Hourmand et al. |
| 2014/0336590 A1 | 11/2014 | Hourmand et al. |
| 2014/0336592 A1 | 11/2014 | Hourmand et al. |
| 2018/0064875 A1 | 3/2018 | Holmqvist |
| 2018/0140781 A1 | 5/2018 | Kemp et al. |
| 2018/0140782 A1 | 5/2018 | Kemp et al. |
| 2018/0256822 A1 | 9/2018 | Hourmand et al. |
| 2019/0201628 A1 | 7/2019 | Hourmand et al. |
| 2019/0201629 A1 | 7/2019 | Hourmand et al. |
| 2019/0374717 A1 | 12/2019 | Swanson et al. |
| 2020/0405960 A1 | 12/2020 | Hourmand et al. |
| 2020/0405961 A1 | 12/2020 | Hourmand et al. |
| 2021/0077743 A1 | 3/2021 | Kemp et al. |
| 2021/0346604 A1 | 11/2021 | Hourmand et al. |
| 2022/0016358 A1 | 1/2022 | Kemp et al. |
| 2022/0054755 A1 | 2/2022 | Hourmand et al. |
| 2022/0054756 A1 | 2/2022 | Hourmand et al. |
| 2022/0054757 A1 | 2/2022 | Hourmand et al. |
| 2022/0054758 A1 | 2/2022 | Hourmand et al. |
| 2024/0207517 A1 | 6/2024 | Fenlon et al. |

FOREIGN PATENT DOCUMENTS

| | | |
|---|---|---|
| CN | 1911467 A | 2/2007 |
| CN | 1977986 A | 6/2007 |
| CN | 2925504 Y | 7/2007 |
| CN | 101022841 A | 8/2007 |
| CN | 101400393 A | 4/2009 |
| CN | 101420995 A | 4/2009 |
| CN | 201213944 Y | 4/2009 |
| CN | 101479004 A | 7/2009 |
| CN | 102014993 A | 4/2011 |
| CN | 102112168 A | 6/2011 |
| CN | 103945879 A | 7/2014 |
| DE | 202009009119 U1 | 12/2009 |
| EA | 012008 B1 | 6/2009 |
| EA | 013934 B1 | 8/2010 |
| EP | 0518416 A1 | 12/1992 |
| EP | 0692272 A1 | 1/1996 |
| EP | 1124601 A1 | 8/2001 |
| EP | 1685865 A1 | 8/2006 |
| EP | 1702643 A2 | 9/2006 |
| EP | 1958654 A1 | 8/2008 |
| EP | 2279771 A1 | 2/2011 |
| EP | 2438952 A1 | 4/2012 |
| EP | 2727617 A1 | 6/2012 |
| EP | 2601992 A1 | 6/2013 |
| EP | 2777684 A1 | 9/2014 |
| EP | 2788052 A1 | 9/2015 |
| EP | 3153197 A1 | 4/2017 |
| FR | 2764195 A1 | 12/1998 |
| FR | 2799654 A1 | 4/2001 |
| GB | 407109 A | 3/1934 |
| GB | 829724 A | 3/1960 |
| GB | 1122592 A | 8/1968 |
| GB | 2388033 A | 11/2003 |
| GB | 2396298 A | 6/2004 |
| GB | 2397767 A | 8/2004 |
| GB | 2447339 A | 9/2008 |
| GB | 2461084 A | 12/2009 |
| GB | 2434317 A | 1/2011 |
| GB | 2471473 A | 1/2011 |
| JP | H08-10324 A | 1/1996 |
| JP | 2002-503127 A | 1/2002 |
| JP | 2002-528182 A | 9/2002 |
| JP | 2003-511159 A | 3/2003 |
| JP | 2005-021247 A | 1/2005 |
| JP | 2005-523121 A | 8/2005 |
| JP | 2005-536300 A | 12/2005 |
| JP | 2006-507903 A | 3/2006 |
| JP | 2006-516901 A | 7/2006 |
| JP | 2007-511299 A | 5/2007 |
| JP | 2008-500854 A | 1/2008 |
| JP | 2009-077943 A | 4/2009 |
| JP | 2009-518080 A | 5/2009 |
| JP | 2009-523587 A | 6/2009 |
| JP | 2009-529395 A | 8/2009 |
| JP | 2011-156005 A | 8/2011 |
| JP | 2011-524763 A | 9/2011 |
| JP | 2014-500086 A | 1/2014 |
| JP | 2014-500089 A | 1/2014 |
| RU | 2068708 C1 | 11/1996 |
| RU | 2172638 C2 | 8/2001 |
| RU | 2311203 C2 | 11/2007 |
| RU | 2363500 C2 | 8/2009 |
| RU | 2012137269 A | 3/2014 |
| WO | WO 1998/035714 A1 | 8/1998 |
| WO | WO 1998/056442 A1 | 12/1998 |
| WO | WO 1999/010030 A2 | 3/1999 |
| WO | WO 1999/022792 A1 | 5/1999 |
| WO | WO 2000/024441 A1 | 5/2000 |
| WO | WO 2001/008727 A1 | 2/2001 |
| WO | WO 2001/060435 A1 | 8/2001 |
| WO | WO 2001/093926 A2 | 12/2001 |
| WO | WO 2002/047746 A1 | 6/2002 |
| WO | WO 2003/013632 A2 | 2/2003 |
| WO | WO 2003/068297 A1 | 8/2003 |
| WO | WO 2003/090822 A1 | 11/2003 |
| WO | WO 2003/099358 A2 | 12/2003 |
| WO | WO 2004/007006 A2 | 1/2004 |
| WO | WO 2004/020026 A1 | 3/2004 |
| WO | WO 2004/050150 A2 | 6/2004 |
| WO | WO 2005/001161 A1 | 1/2005 |
| WO | WO 2005/002650 A1 | 1/2005 |
| WO | WO 2005/070481 A1 | 8/2005 |
| WO | WO 2005/083614 A2 | 9/2005 |
| WO | WO 2005/115506 A1 | 12/2005 |
| WO | WO 2005/115507 A1 | 12/2005 |
| WO | WO 2006/047810 A1 | 5/2006 |
| WO | WO 2006/085176 A1 | 8/2006 |
| WO | WO 2006/106291 A1 | 10/2006 |
| WO | WO 2006/106295 A1 | 10/2006 |
| WO | WO 2007/056792 A1 | 5/2007 |
| WO | WO 2007/083115 A1 | 7/2007 |
| WO | WO 2007/104636 A1 | 9/2007 |
| WO | WO 2007/129106 A2 | 11/2007 |
| WO | WO 2008/000827 A1 | 1/2008 |
| WO | WO 2009/019437 A1 | 2/2009 |
| WO | WO 2009/022132 A2 | 2/2009 |
| WO | WO 2009/153541 A2 | 12/2009 |
| WO | WO 2010/072644 A1 | 7/2010 |
| WO | WO 2010/097116 A1 | 9/2010 |
| WO | WO 2010/115822 A2 | 10/2010 |
| WO | WO 2010/136076 A1 | 12/2010 |
| WO | WO 2010/136077 A1 | 12/2010 |
| WO | WO 2010/136078 A1 | 12/2010 |
| WO | WO 2010/147553 A1 | 12/2010 |
| WO | WO 2011/000570 A1 | 1/2011 |
| WO | WO 2011/001161 A1 | 1/2011 |
| WO | WO 2011/101378 A1 | 8/2011 |
| WO | WO 2011/109205 A2 | 9/2011 |
| WO | WO 2012/073032 A1 | 6/2012 |
| WO | WO 2012/089445 A1 | 7/2012 |
| WO | WO 2012/164403 A2 | 12/2012 |
| WO | WO 2013/072182 A1 | 5/2013 |
| WO | WO 2013/083613 A1 | 6/2013 |
| WO | WO 2013/083614 A1 | 6/2013 |
| WO | WO 2014/140152 A1 | 9/2014 |
| WO | WO 2019/074788 A1 | 4/2019 |

(56) References Cited

FOREIGN PATENT DOCUMENTS

| WO | WO 2020/190529 A1 | 9/2020 |
| WO | WO 2021/008839 A1 | 1/2021 |

OTHER PUBLICATIONS

International Search Report and Written Opinion in International Appln. No. PCT/EP2014/054922, mailed on Apr. 1, 2014, 10 pages.

* cited by examiner

MEDICAMENT CONTAINER CARRIER AND ADAPTER

CROSS-REFERENCE TO RELATED APPLICATIONS

This application is a continuation application of U.S. application Ser. No. 17/564,354, filed on Dec. 29, 2021, which is a continuation application of U.S. application Ser. No. 14/775,316, filed on Sep. 11, 2015, now U.S. Pat. No. 11,235,102, which is a U.S. national stage application under 35 USC § 371 of International Application No. PCT/EP2014/054922, filed on Mar. 13, 2014, which claims priority to European Patent Application No. 13159253.7, filed on Mar. 14, 2013, the entire contents of which are incorporated herein by reference.

TECHNICAL FIELD

The invention relates to an adapter for a medicament container carrier.

BACKGROUND OF THE INVENTION

In a conventional medicament delivery device (e.g., an autoinjector), a pre-filled medicament container (e.g., syringe) is housed in a carrier which is axially movable to achieve needle penetration in an injection site and, optionally, needle withdrawal. A conventional carrier is typically sized and shaped to retain a medicament container of a predetermined size. In order to increase a dose that can be administered by the delivery device, a larger carrier would be necessary to accommodate a larger medicament container. However, a size and shape of the delivery device may not provide space for the larger medicament container. Thus, an entirely different delivery device may be necessary for different dosage amounts.

Accordingly, there is a need for a carrier and an adapter that allows the carrier to accommodate medicament containers of various sizes.

SUMMARY OF THE INVENTION

It is an object of the present invention to provide a medicament container carrier and an adapter for the medicament container carrier.

In an exemplary embodiment, a medicament container carrier adapted to hold a first medicament container having a first predetermined size and capable of containing more than a first volume of a medicament according to the present invention comprises a body, and an adapter coupled to the body. The adapter is adapted to hold a second medicament container having a second predetermined size different from the first predetermined size and capable of containing no more than the first volume of the medicament.

In an exemplary embodiment, the first volume is approximately 2 mL.

In an exemplary embodiment, the adapter includes a distal rib adapted to abut a distal end of the second medicament container.

In an exemplary embodiment, the adapter includes at least one opening providing visual access to the second medicament container.

In an exemplary embodiment, the adapter includes at least one resilient arm adapted to engage the second medicament container. The arm includes a first ramp adapted to engage a distal face of a flange to deflect the arm in a first radial direction. The arm includes a first abutment surface adapted to engage the flange to prevent rotation of the second medicament container relative to the adapter and a second abutment surface adapted to engage the flange to prevent axial displacement of the second medicament container relative to the adapter. The arm includes a second ramp adapted to engage an engagement element on the body to deflect the arm in a second radial direction. The arm includes a third abutment surface adapted to abut a proximal stop in the body to prevent axial displacement of the adapter relative to the body, and a fourth abutment surface adapted to engage a restricting surface in the body to prevent rotation of the adapter relative to the body. The proximal stop is formed in an aperture on the body.

In an exemplary embodiment, the first medicament container and the second medicament container are each one of a pre-filled syringe and a medicament cartridge.

In an exemplary embodiment, a medicament delivery device according to the present invention comprises a housing, and a medicament container carrier according to the exemplary embodiments described herein. The medicament container carrier may be slidably disposed in the housing.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, do not limit the present invention, and wherein.

Corresponding parts are marked with the same reference symbols in all figures.

DETAILED DESCRIPTION

Figure 1:
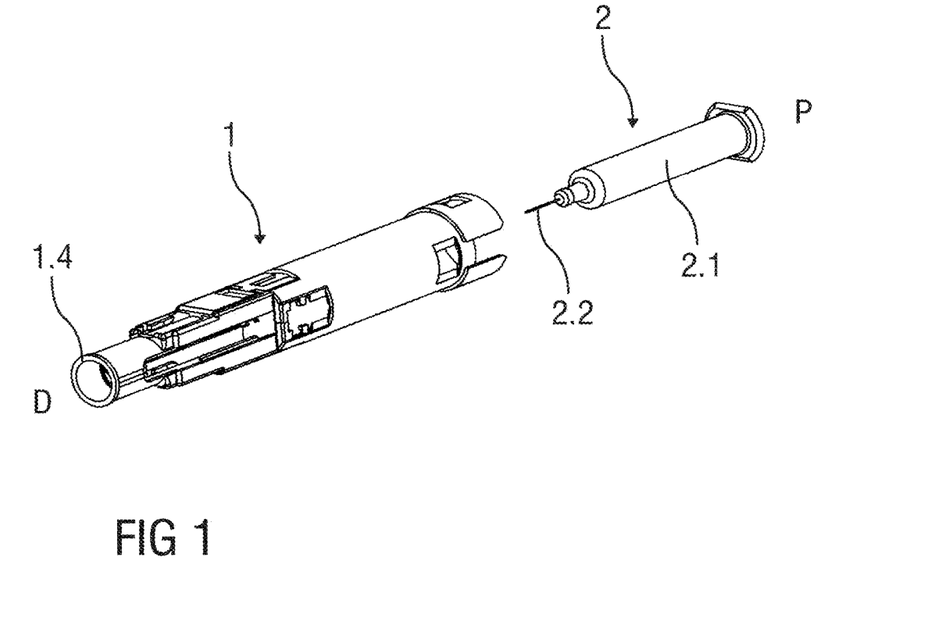
FIG. 1 is a schematic perspective exploded view of an exemplary embodiment of a container carrier and a first medicament container according to the present invention.

FIG. 1 is a schematic perspective exploded view of an exemplary embodiment of a container carrier 1 having a body adapted to hold a first medicament container 2 according to the present invention. The first medicament container 2, which may be a syringe, an ampoule, a cartridge, etc., has a first predetermined size (e.g., length, diameter, etc.) and contains up to a first maximum amount of a medicament. For example, the first medicament container 2 may be a prefilled syringe containing a 2 mL dose of a medicament.

In an exemplary embodiment, the first medicament container 2 comprises a medicament container body 2.1, a needle 2.2 mounted to a distal end of the medicament container body 2.1 and in fluid communication with a cavity defined within the medicament container body 2.1 for containing a medicament, and a stopper (not illustrated) disposed within the cavity near a proximal end of the medicament container body 2.1, wherein the stopper proximally seals the cavity and can be axially displaced within the cavity for expelling the medicament through the needle 2.2. The needle 2.2 may fixed to the container body 2.1 or may be removably coupled thereto. In the latter exemplary embodiment, the needle 2.2 may be a double-tipped needle and the distal end of the body 2.1 may include a septum which receives a proximal tip of the needle 2.2. In the figures, "D" refers to the distal direction, and "P" refers to the proximal direction.

Figure 2:
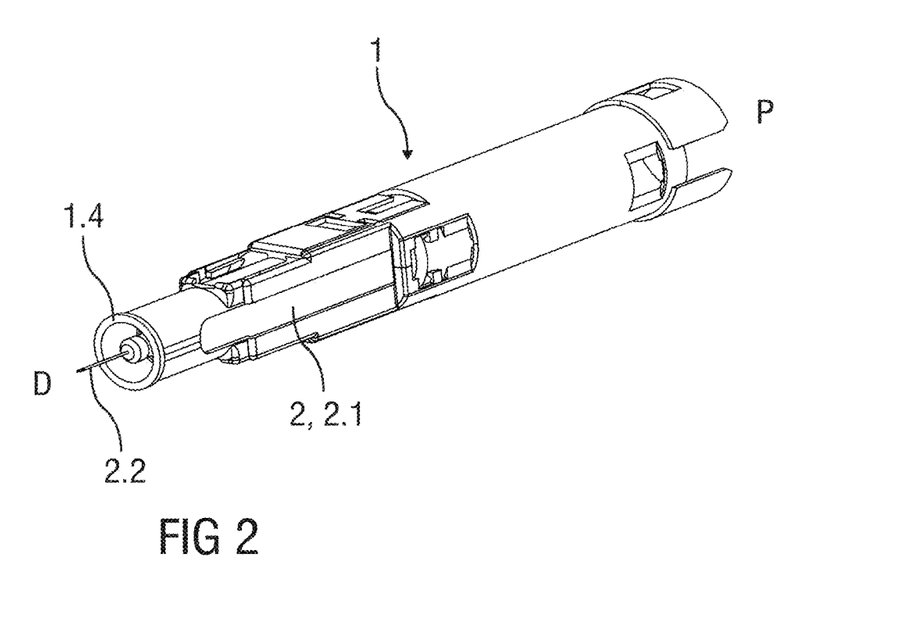
FIG. 2 is a schematic perspective view of an exemplary embodiment of a container carrier coupled to a first medicament container according to the present invention.

FIG. 2 is a schematic perspective view of an exemplary embodiment of the container carrier 1 with the first medicament container 2 coupled thereto. The first medicament container 2 may be inserted into a proximal opening of the container carrier 1 and moved distally until it abuts a distal stop. A retention mechanism (e.g., snaps, clips, locks, etc.) in the container carrier 1 may engage a proximal end (e.g., flange(s)) of the first medicament container 2 to prevent the first medicament container 2 from translating axially relative to the container carrier 1 and/or rotating relative to the container carrier 1.

Figure 3:
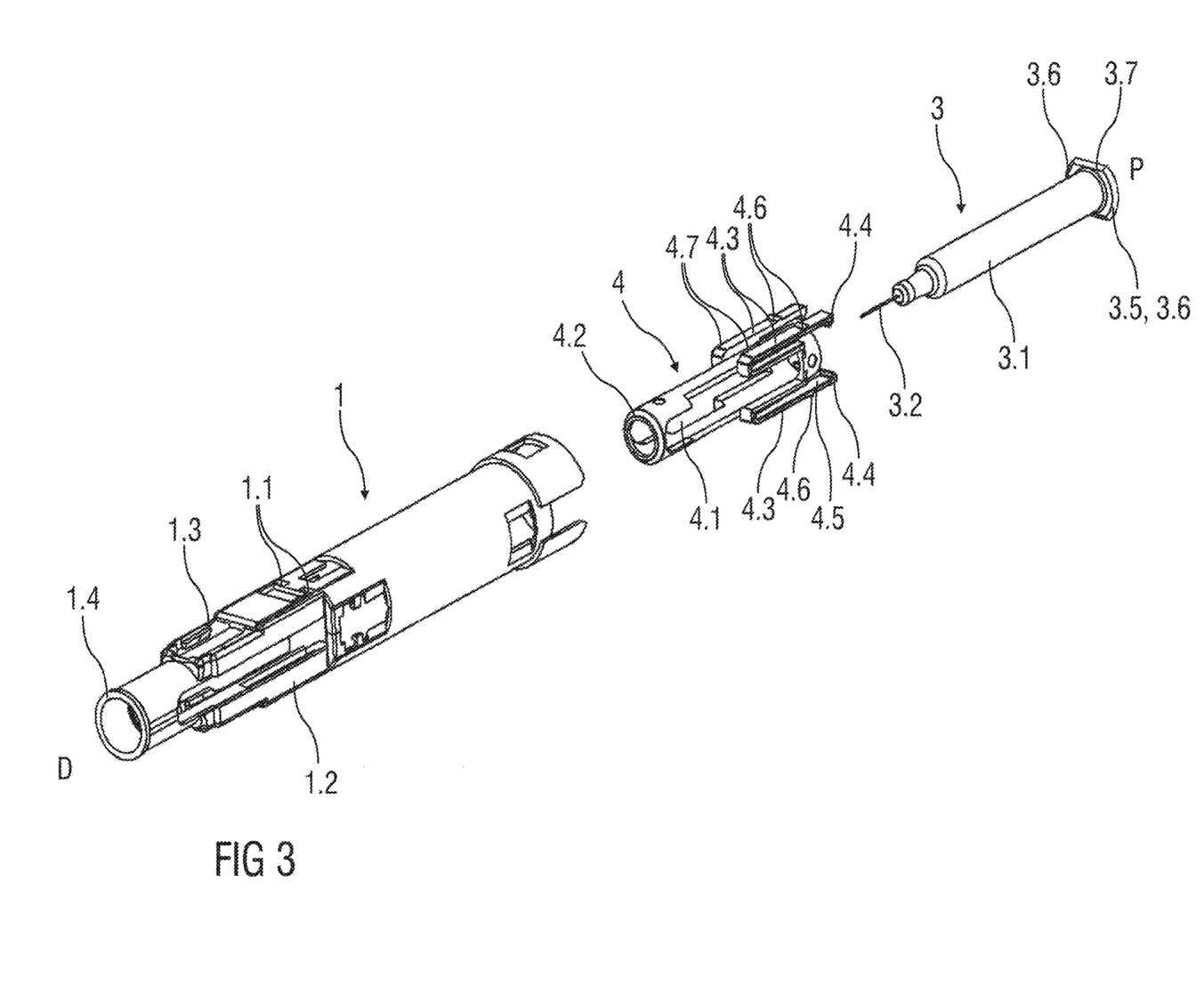
FIG. 3 is a schematic perspective exploded view of an exemplary embodiment of a container carrier, an adapter and a second medicament container according to the present invention.
Figure 4:
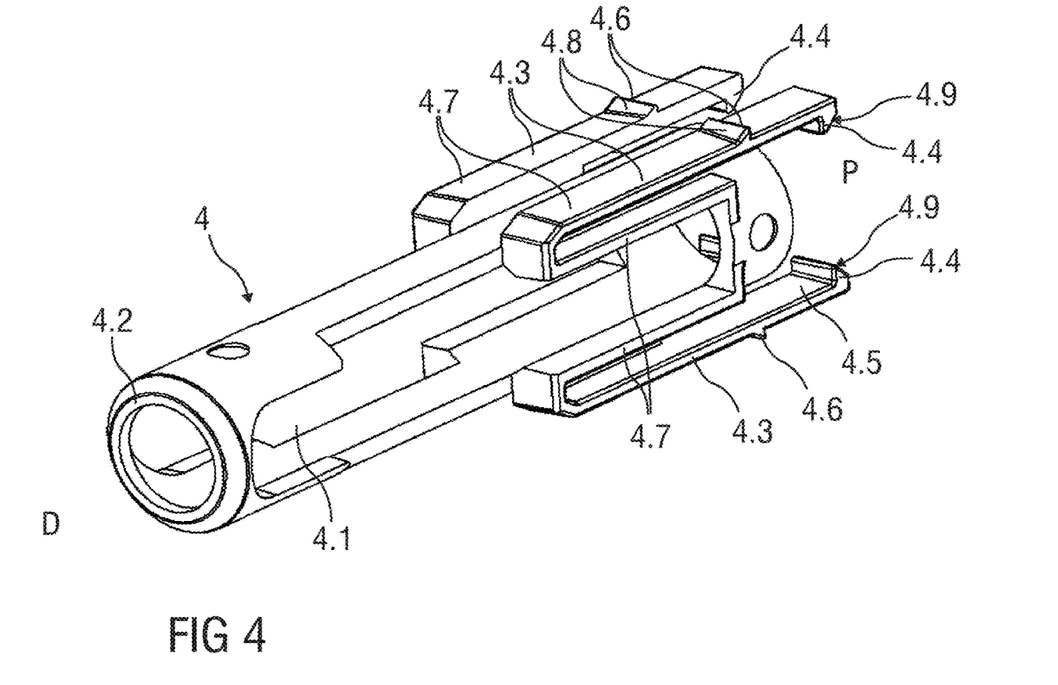
FIG. 4 is a schematic perspective view of an exemplary embodiment of an adapter according to the present invention.

FIG. 3 is a schematic perspective exploded view of an exemplary embodiment of the container carrier 1, an adapter 4 and a second medicament container 3. FIG. 4 is a schematic perspective view of an exemplary embodiment of the adapter 4.

In an exemplary embodiment, the adapter 4 is designed to engage a second medicament container 3 having a second predetermined size smaller than the first predetermined size of the first medicament container 2. The adapter 4 may further be designed to engage the container carrier 1. The second medicament container 3 comprises a medicament container body 3.1, a needle 3.2 mounted to a distal end of the medicament container body 3.1 and in fluid communication with a cavity defined within the medicament container body 3.1 for containing a medicament, and a stopper (not illustrated) disposed within the cavity near a proximal end of the medicament container body 3.1, wherein the stopper proximally seals the cavity and can be axially displaced within the cavity for expelling the medicament through the needle 3.2. The needle 3.2 may fixed to the container body 3.1 or may be removably coupled thereto. In the latter exemplary embodiment, the needle 3.2 may be a double-tipped needle and the distal end of the body 3.1 may include a septum which receives a proximal tip of the needle 3.2. A flange 3.5 may be arranged at a proximal end of medicament container body 3.1. In an exemplary embodiment, the flange 3.5 comprises two arc sections 3.6 connected by two straight sections 3.7.

In an exemplary embodiment, the adapter 4 may be used to allow a medicament delivery device (e.g., a pen injector, an auto-injector, etc.) to accommodate various medicament container sizes. The adapter 4 may allow the usage of a common delivery device for different medicament container sizes. Therefore, a reduction in device costs and consistency in medicament administration may be achieved.

In an exemplary embodiment, the adapter 4 is adapted to retain the second medicament container 3 such that the second medicament container 3 is axially and rotationally fixed within the adapter 4. The adapter 4 is also adapted to be retained within the container carrier 1 such that the adapter 4 is axially and rotationally fixed within the container carrier 1. Preventing rotation of the second medicament container 3 prevents the needle 3.2 from rotating during an injection thus reducing the risk for bending and distorting the needle 3.2 which may otherwise result in pain. Preventing axial movement of the medicament container 3 in a proximal direction P also prevents the second medicament container 3 from being pushed in the proximal direction P relative to the adapter 4 and the container carrier 1 upon contact of the needle 3.2 with an injection site.

In an exemplary embodiment as shown in FIG. 4, the adapter 4 may be sized and/or shaped to telescopically engage the container carrier 1 and the second medicament container 3. For example, the adapter 4 may have an outer geometry which corresponds to an inner shape of the container carrier 1 and an inner geometry which corresponds to the second predetermined size/shape of the second medicament container 3. A distal rib 4.2 formed on a distal end of the adapter 4 may be adapted to abut the distal end of the container body 3.1 to prevent distal movement of the second medicament container 3 beyond the distal rib 4.2.

In an exemplary embodiment, the adapter 4 may include one or more lateral openings 4.1 for allowing inspection of the contents and state of the second medicament container 3. In another exemplary embodiment, the adapter 4 may be made from a transparent/translucent material to provide visual access to the contents of the second medicament container 3.

Figure 5:
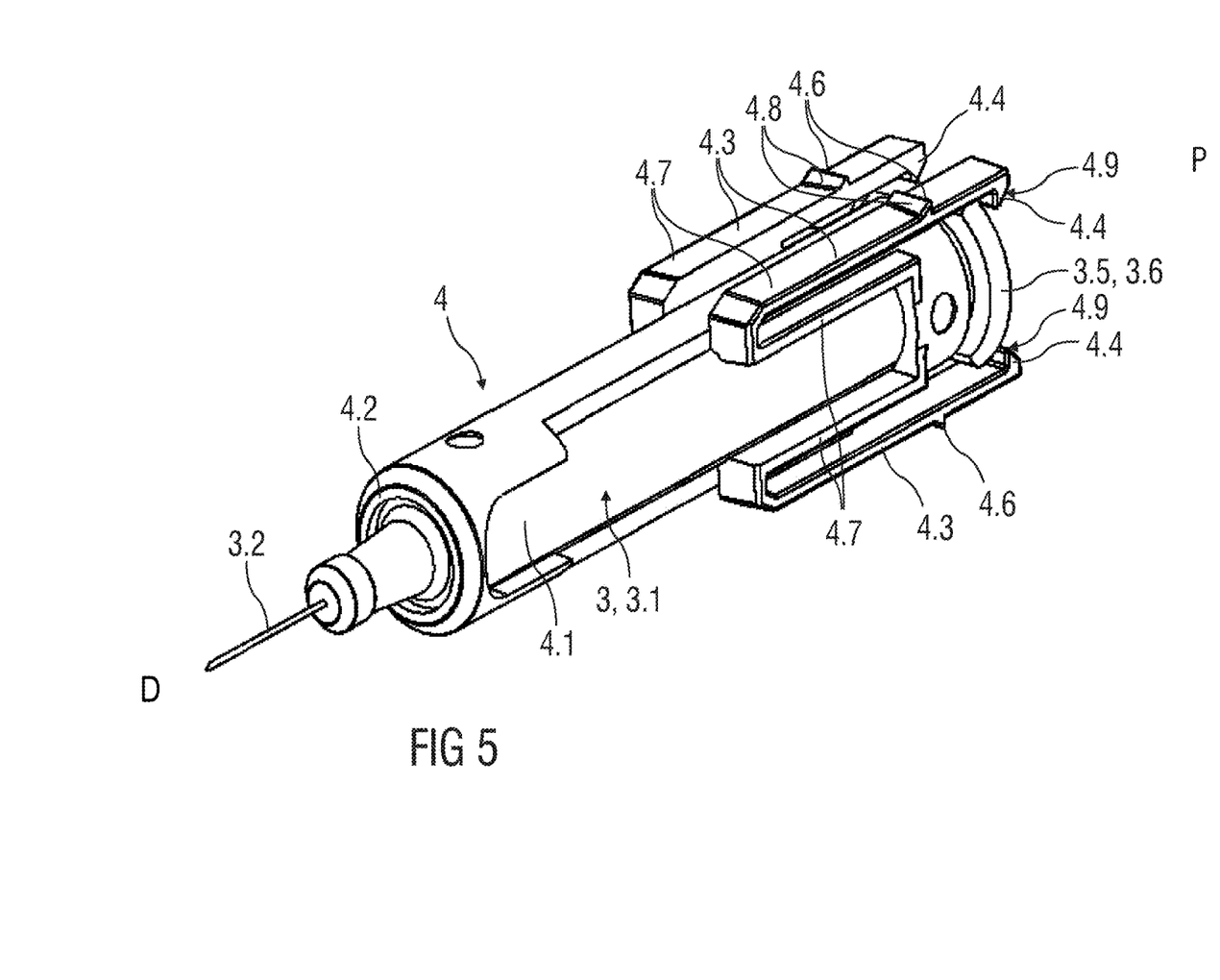
FIG. 5 is a schematic perspective view of an exemplary embodiment of a second medicament container coupled to an adapter according to the present invention.

In an exemplary embodiment, the adapter 4 may comprise at least one resilient arm 4.3 extending proximally and adapted to engage a proximal portion (e.g., the flange 3.5) of the container body 3.1. In the exemplary embodiment shown in FIG. 4, the adapter 4 includes four resilient arms 4.3. The arm 4.3 may include features to facilitate insertion and retention of the second medicament container 3. For example, a proximal end of the arm 4.3 may include a first ramp 4.9 which is adapted to engage the flange 3.5 (e.g., the straight section 3.7) when the second medicament container 3 is inserted into the adapter 4. As the flange 3.5 engages the first ramp 4.9, the arm 4.3 is deflected in a first radial direction until the flange 3.5 bypasses the ramped face 4.9. As shown in FIG. 5, when the arm 4.3 returns to a non-deflected position, a first abutment surface 4.5 may engage the flange 3.5 (e.g., straight section 3.7) and thereby prevent the second medicament container 3 from rotating relative to the adapter 4, and a second abutment surface 4.4 may abut a proximal face of the flange 3.5 and thereby prevent the second medicament container 3 from moving axially relative to the adapter 4.

Referring back to the exemplary embodiment shown in FIG. 4, the resilient arm 4.3 may include a second ramp 4.8, a third abutment surface 4.6, and a fourth abutment surface 4.7 which facilitate insertion and retention of the adapter 4 by the container carrier 1. For example, the second ramp 4.8 may be disposed on a radially outer surface of the arm 4.3. When the adapter 4 is inserted into the container carrier 1, the second ramp 4.8 may engage an element or an aperture 1.1 on the container carrier 1, which causes the arm 4.3 to deflect in a second radial direction (opposite the first radial direction) until the second ramp 4.8 bypasses the element. When the arm 4.3 returns to the non-deflected position, the third abutment surface 4.6 may engage a proximal stop in the container carrier 1 and thereby prevent axial displacement of the adapter 4 relative to the container carrier 1. The fourth abutment surface 4.7 may engage a surface or element in the container carrier 1 to prevent rotation of the adapter 4 relative to the container carrier 1.

Figure 6:
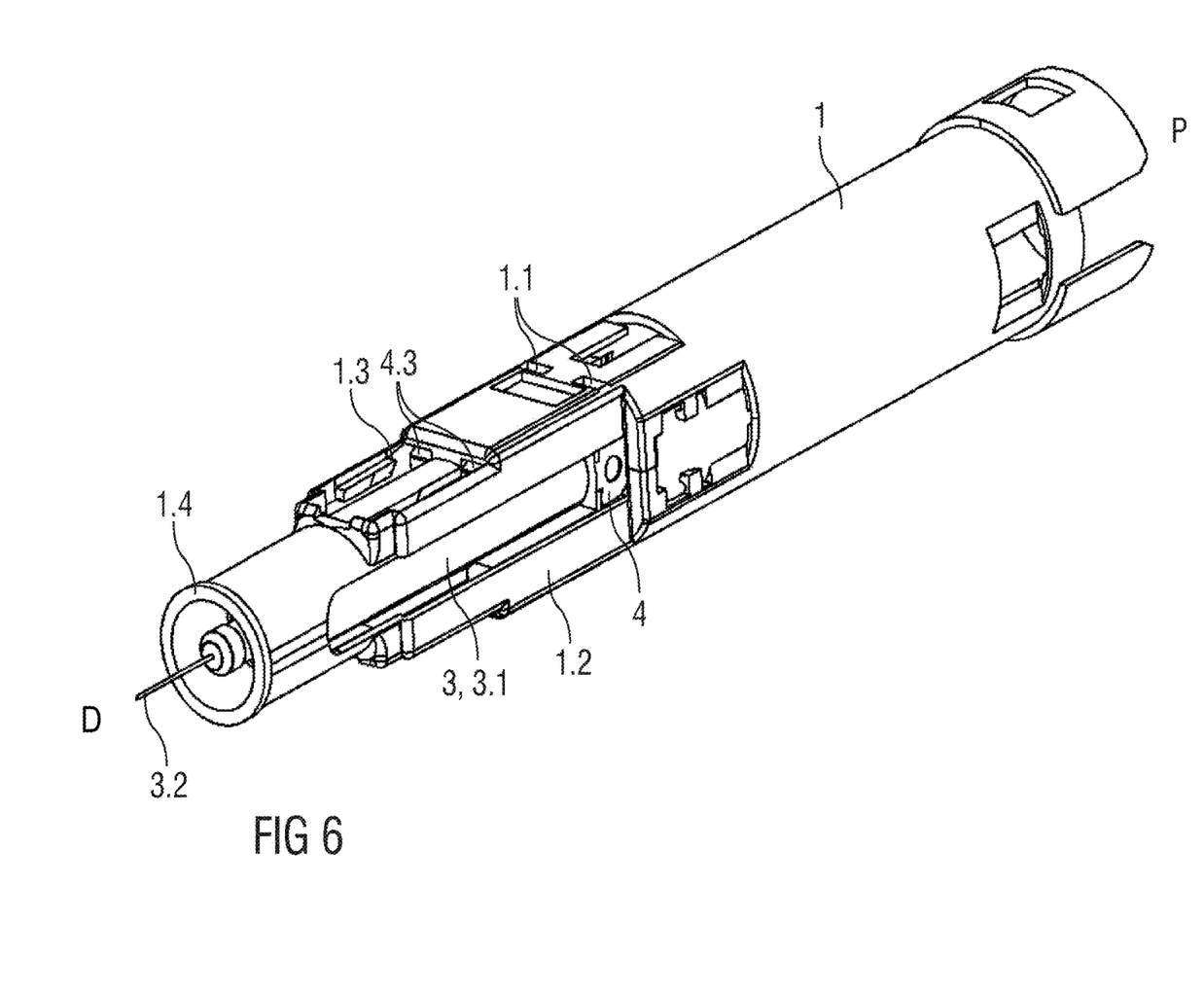
FIG. 6 is a schematic perspective view of an exemplary embodiment of a container carrier coupled to an adapter and a second medicament container according to the present invention.
Figure 7:
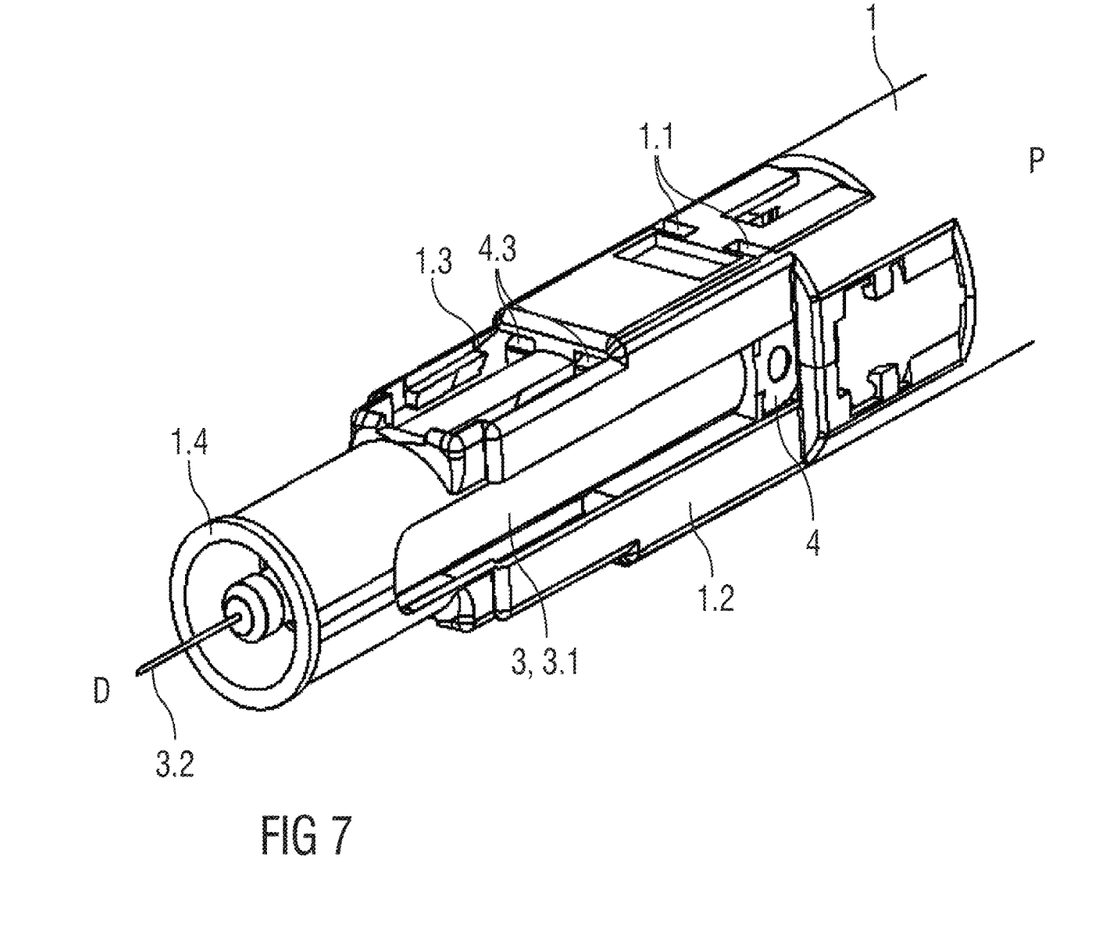
FIG. 7 is a schematic perspective detail view of an exemplary embodiment of a container carrier coupled to an adapter and a second medicament container according to the present invention.

The second medicament container 3 may be assembled with the container carrier 1 as shown in FIGS. 6 and 7 in at least two ways. In a first exemplary process, the adapter 4 may be inserted into the container carrier 1 and translated distally until it abuts a distal stop 1.3 and the third abutment surface 4.6 abuts proximal stop. The second medicament container 3 may then be inserted into the adapter 4 and translated distally until it abuts the distal rib 4.2 and the second abutment surface 4.4 abuts the flange 3.5. In a second exemplary process, the second medicament container 3 may be inserted into the adapter 4, and the adapter 4 may then be inserted into the container carrier 1.

In an exemplary embodiment, the first medicament container 2 may be adapted to contain greater than approximately 2 mL of a medicament, and the second medicament container may be adapted to contain less than approximately 2 mL of a medicament.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. An auto-injector comprising:
a syringe carrier;
a syringe comprising a barrel that extends from a distal needle of the syringe to a proximal flange of the syringe, the barrel defining an opening for a volume of a medicament; and
a translucent syringe support disposed in the syringe carrier, the translucent syringe support comprising:
one or more first abutment surfaces engaged to diametrically opposite portions of a proximal side of the proximal flange of the syringe to limit proximal movement of the syringe relative to the translucent syringe support;
a second abutment surface in sliding engagement to an inner surface of the syringe carrier; and
a third abutment surface that is distal to a distal side of the proximal flange of the syringe to limit distal movement of the syringe relative to the translucent syringe support,
wherein the auto-injector is configured to dispense the volume of the medicament through the distal needle of the syringe by distally moving a stopper within the barrel of the syringe.

2. The auto-injector of claim 1, wherein the volume of the medicament is greater than 0 milliliters and less than 2 milliliters.

3. The auto-injector of claim 1, wherein the translucent syringe support comprises a pair of fourth abutment surfaces configured to limit a rotation of the syringe relative to the syringe carrier, the pair of fourth abutment surfaces facing one another and being perpendicular to the one or more first abutment surfaces.

4. The auto-injector of claim 3, wherein the pair of fourth abutment surfaces of the translucent syringe support are in direct contact to the syringe.

5. The auto-injector of claim 1, wherein the third abutment surface of the translucent syringe support is in direct contact to the syringe.

6. The auto-injector of claim 1, wherein the distal side of the proximal flange of the syringe is proximally spaced from the translucent syringe support.

7. The auto-injector of claim 1, wherein the translucent syringe support comprises an axially-extending portion located radially outward of the proximal flange of the syringe, the axially-extending portion extending from the distal side of the proximal flange of the syringe to the proximal side of the proximal flange of the syringe.

8. The auto-injector of claim 7, wherein the translucent syringe support comprises a proximal portion extending radially inward from a proximal end of the axially-extending portion on the proximal side of the proximal flange, the proximal portion defining the one or more first abutment surfaces.

9. The auto-injector of claim 8, wherein the one or more first abutment surfaces extend in a plane that is perpendicular to a longitudinal axis of the syringe along a substantial entirety of the one or more first abutment surfaces.

10. An auto-injector comprising:
a syringe carrier; and
a translucent syringe support configured to be disposed in the syringe carrier, the translucent syringe support comprising:
one or more first abutment surfaces configured to engage diametrically opposite portions of a proximal side of a proximal flange of a syringe to limit proximal movement of the syringe relative to the translucent syringe support when the proximal flange of the syringe is disposed in the translucent syringe support;
a second abutment surface configured to slidably engage an inner surface of the syringe carrier when the translucent syringe support is disposed in the syringe carrier; and
a third abutment surface that is distal to a distal side of the proximal flange of the syringe to limit distal movement of the syringe relative to the translucent syringe support when the proximal flange of the syringe is disposed in the translucent syringe support.

11. The auto-injector of claim 10, wherein the translucent syringe support comprises a pair of fourth abutment surfaces configured to limit a rotation of the syringe relative to the syringe carrier when the proximal flange of the syringe is disposed in the translucent syringe support.

12. The auto-injector of claim 11, wherein the pair of fourth abutment surfaces face one another.

13. The auto-injector of claim 11, wherein the pair of fourth abutment surfaces are perpendicular to the one or more first abutment surfaces.

14. The auto-injector of claim 11, wherein the pair of fourth abutment surfaces of the translucent syringe support are configured to directly contact the syringe when the proximal flange of the syringe is disposed in the translucent syringe support.

15. The auto-injector of claim 10, wherein the auto-injector is configured such that a distal needle of the syringe is distal to a distal end of the syringe carrier when the proximal flange of the syringe is disposed in the translucent syringe support and the translucent syringe support is disposed in the syringe carrier.

16. The auto-injector of claim 15, wherein the auto-injector is configured such that a proximal end of the translucent syringe support is proximal to a proximal end of the syringe carrier when the translucent syringe support is disposed in the syringe carrier.

17. The auto-injector of claim 10, comprising the syringe, the syringe containing a volume of a medicament greater than 0 milliliters and less than 2 milliliters.

18. The auto-injector of claim 17, wherein the proximal flange of the syringe comprises one or more circular portions.

19. An auto-injector comprising:
a housing;
a syringe carrier disposed in the housing; and
a translucent syringe support disposed in the syringe carrier, the translucent syringe support comprising:
a first abutment surface configured to engage a proximal side of a proximal flange of a syringe to limit proximal movement of the syringe relative to the translucent syringe support when the proximal flange of the syringe is disposed in the translucent syringe support; and
a second abutment surface engaged to an inner surface of the syringe carrier, the second abutment surface being radially outward of the first abutment surface and extending in a direction substantially perpendicular to the first abutment surface.

20. The auto-injector of claim 19, wherein the translucent syringe support is configured to limit distal movement of the syringe relative to the translucent syringe support when the proximal flange of the syringe is disposed in the translucent syringe support with the proximal side of the proximal flange engaged to the first abutment surface of the translucent syringe support.

21. The auto-injector of claim 20, wherein the translucent syringe support and the syringe are configured such that a distal side of the proximal flange is proximally spaced from the translucent syringe support when the proximal flange of the syringe is disposed in the translucent syringe support with the proximal side of the proximal flange engaged to the first abutment surface of the translucent syringe support.

22. The auto-injector of claim 20, wherein the translucent syringe support is configured such that a proximal portion of the translucent syringe support at least partially surrounds diametrically opposite sides of the proximal flange of the syringe when the proximal flange of the syringe is disposed in the translucent syringe support with the proximal side of the proximal flange engaged to the first abutment surface of the translucent syringe support.

23. The auto-injector of claim 19, comprising the syringe disposed in the translucent syringe support, the syringe containing a volume of a medicament greater than 0 milliliters and less than 2 milliliters.

24. A translucent syringe support for a syringe, the translucent syringe support comprising:
one or more first abutment surfaces configured to engage diametrically opposite portions of a proximal side of a proximal flange of the syringe to limit proximal movement of the syringe relative to the translucent syringe support when the syringe is disposed in the translucent syringe support;
a second abutment surface configured to slidably engage an inner surface of a syringe carrier of an auto-injector for moving the syringe carrier and the syringe within the auto-injector; and
a third abutment surface that is distal to a distal side of the proximal flange of the syringe to limit distal movement of the syringe relative to the translucent syringe support when the syringe is disposed in the translucent syringe support.

25. The translucent syringe support of claim 24, comprising an axially-extending portion configured to be radially outward of the proximal flange of the syringe and extending from the distal side of the proximal flange of the syringe to the proximal side of the proximal flange of the syringe when the syringe is disposed in the translucent syringe support.

26. The translucent syringe support of claim 25, comprising a proximal portion extending radially inward from a proximal end of the axially-extending portion on the proximal side of the proximal flange, a distal side of the proximal portion defining the one or more first abutment surfaces.

27. The translucent syringe support of claim 26, wherein a substantial entirety of the one or more first abutment surfaces extend in a plane that is perpendicular to a longitudinal axis of the syringe.

28. The translucent syringe support of claim 24, wherein the translucent syringe support comprises a pair of fourth abutment surfaces configured to limit a rotation of the syringe relative to the syringe carrier when the syringe is disposed in the translucent syringe support.

29. The translucent syringe support of claim 28, wherein the pair of fourth abutment surfaces face one another and are perpendicular to the one or more first abutment surfaces.

30. The translucent syringe support of claim 24, wherein the distal side of the proximal flange of the syringe is proximally spaced from the translucent syringe support when the syringe is disposed in the translucent syringe support with the proximal side of the proximal flange of the syringe engaged to the one or more first abutment surfaces.

* * * * *